United States Patent
Sanders et al.

(10) Patent No.: US 10,173,970 B2
(45) Date of Patent: Jan. 8, 2019

(54) METHOD FOR PRODUCING 1,5-PENTANEDIISOCYANATE IN THE GAS PHASE

(71) Applicant: Covestro Deutschland AG, Leverkusen (DE)

(72) Inventors: Josef Sanders, Leverkusen (DE); Martin Ehrig, Leverkusen (DE); Reinhard Halpaap, Odenthal (DE); Manfred Keller-Killewald, Dormagen (DE); Armin Schymura, Neuss (DE); Dietmar Wastian, Dormagen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/512,115

(22) PCT Filed: Sep. 18, 2015

(86) PCT No.: PCT/EP2015/071438
§ 371 (c)(1),
(2) Date: Mar. 17, 2017

(87) PCT Pub. No.: WO2016/042125
PCT Pub. Date: Mar. 24, 2016

(65) Prior Publication Data
US 2017/0283370 A1    Oct. 5, 2017

(30) Foreign Application Priority Data
Sep. 19, 2014 (EP) .................................. 14185564

(51) Int. Cl.
*C07C 263/10* (2006.01)
*C07C 265/14* (2006.01)

(52) U.S. Cl.
CPC .......... *C07C 263/10* (2013.01); *C07C 265/14* (2013.01)

(58) Field of Classification Search
CPC .................................................. C07C 263/10
See application file for complete search history.

(56) References Cited

U.S. PATENT DOCUMENTS

| | | |
|---|---|---|
| 4,847,408 A | 7/1989 | Frosch et al. |
| 6,706,913 B2 | 3/2004 | Leimkühler et al. |
| 6,838,578 B2 | 1/2005 | Leimkühler et al. |
| 6,930,199 B2 | 8/2005 | Meyn et al. |
| 6,974,880 B2 | 12/2005 | Biskup et al. |
| 7,019,164 B2 | 3/2006 | Friedrich et al. |
| 8,044,166 B2 | 10/2011 | Fiene et al. |
| 8,258,337 B2 | 9/2012 | Woelfert et al. |
| 8,692,016 B2 | 4/2014 | Sanders et al. |
| 8,957,245 B2 | 2/2015 | Olbert et al. |
| 9,371,413 B2 | 6/2016 | Nakagawa et al. |
| 2009/0221846 A1* | 9/2009 | Wolfert ............... B01F 5/0453 560/347 |
| 2010/0210870 A1* | 8/2010 | Olbert ................. C07C 263/10 560/347 |
| 2013/0079486 A1* | 3/2013 | Hidesaki ............ C07C 263/10 528/65 |

FOREIGN PATENT DOCUMENTS

| | | |
|---|---|---|
| DE | 2625075 A1 | 12/1977 |
| GB | 1225450 | 3/1971 |

OTHER PUBLICATIONS

T. Lesiak, K. Seyda, Preparation of Aliphatic Diisocyanates without using of Phosgene, Journal Für Praktische Chemie (Leipzig), 1979, 321 (1), 161-163.
W. Siefken, Mono- und Polyisocyanate, Justus Liebigs Annalen Chem. 562, 1949, p. 75 ff., (p. 122).

* cited by examiner

*Primary Examiner* — Ana Z Muresan
(74) *Attorney, Agent, or Firm* — John E. Mrozinski, Jr.

(57) ABSTRACT

The invention relates to a method for producing 1,5-pentanediisocyanate (PDI) by reacting 1,5-pentanediamine (PDA) with phosgene in the gas phase.

11 Claims, No Drawings

METHOD FOR PRODUCING 1,5-PENTANEDIISOCYANATE IN THE GAS PHASE

CROSS-REFERENCE TO RELATED APPLICATIONS

This Application is a National Phase Application of PCT/EP2015/071438, filed Sep. 18, 2015, which claims priority to European Application No. 14185564.3, filed Sep. 19, 2014, both of which are incorporated herein by reference.

FIELD OF THE INVENTION

The invention relates to a process for preparing pentane 1,5-diisocyanate (PDI) by reacting pentane-1,5-diamine (PDA) with phosgene in the gas phase.

BACKGROUND OF THE INVENTION

Isocyanates are produced in large volumes and serve mainly as starting materials for production of polyurethanes. Since the standard monomeric diisocyanates have a relatively low molar mass and generally correspondingly higher vapor pressure, polyisocyanates prepared therefrom are used for reasons of occupational health, particularly in paint production. These polyisocyanates are, for example, uretdiones, isocyanurates, iminooxadiazinediones, biurets, urethanes, allophanates or ureas, which are prepared from the monomeric diisocyanates by di- and trimerization, generally in the presence of catalysts. For this purpose, however, particularly high demands are placed on the purity of the monomers, since the secondary components typically present therein reduce the activity of the catalysts, significantly in some cases. It is therefore necessary to employ higher catalyst concentrations or longer reaction times, which distinctly worsens the quality of the resulting polyisocyanates, for example with regard to color and storage stability.

It is therefore desirable that a minimum level of secondary components have formed at the early monomeric diisocyanate production stage, in order then to limit the cost and inconvenience associated with the removal or minimization thereof, for example by fractional distillation.

In the case of pentane 1,5-diisocyanate, particularly the chlorinated secondary components 5-chloropentyl isocyanate (CPI), N-carbamoylpiperidine ("C6-Im") and the two isomeric N-carbamoyltetrahydropyridines ("C6-Az") are formed. While the formation of CPI reduces the yield and CPI is troublesome as a chain terminator in further processing because of its monofunctionality, particularly the C6-Im and C6-Az components, which contribute to what is called the HC (hydrolyzable chlorine) value, impair the catalysis in the further processing of PDI to give polyisocyanates, and so the HC value of the monomers used for preparation of the polyisocyanates should always be <100 and preferably <50 ppm.

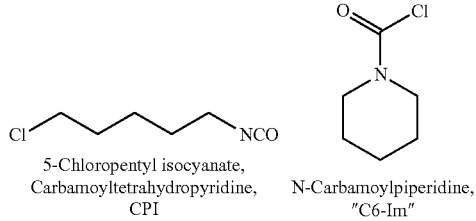

5-Chloropentyl isocyanate, Carbamoyltetrahydropyridine, CPI

N-Carbamoylpiperidine, "C6-Im"

-continued

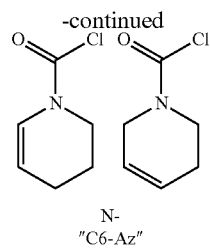

N-"C6-Az"

In the PDI which is used for preparation of polyisocyanates, the concentration of CPI should be <0.3% and the sum total of the concentrations of C6-Im and C6-Az should not exceed 400 ppm, preferably 200 ppm. Since the removal of C6-Im and C6-Az from the PDI, for example by distillation, is very difficult and inconvenient, the concentration thereof in the crude materials as well should not be significantly higher.

The preparation of pentane 1,5-diisocyanate (PDI) from pentane-1,5-diamine(PDA) is known per se and can be effected in a phosgene-free manner (T. Lesiak, K. Seyda, Journal für Praktische Chemie (Leipzig), 1979, 321 (1), 161-163) or by reaction with phosgene (for example W. Siefken, Justus Liebigs Ann. Chem. 562, 1949, p. 75 ff., (p. 122) or DE 2 625 075 A1).

In the case of the above-cited phosgene-free preparation, PDA is first reacted with formic acid to give the formamide and then oxidized with halogen in the presence of tertiary amines to give PDI. A disadvantage of this process is that it is a complex two-stage process, wherein by-products are formed to a considerable extent. The resultant yield losses and the high purification complexity required reduce the economic viability of this process. DE 2 625 075 A1 claims a process for preparing carbamoyl chlorides and isocyanates, characterized in that salts of primary amines are reacted with phosgene in solid form in the presence of a liquid at elevated temperature in a rotary oven, a paddle drier or a fluidized bed reactor. A disadvantage of this process is that this too is a multistage process in which, in the first stage, an amine salt is first prepared in a solvent which then has to be removed again prior to the reaction with phosgene, for example by filtration or centrifugation and subsequent drying. This is time-consuming and costly and reduces the economic viability of this process.

DE 1 900 514 A1 describes the two-stage preparation of PDI from caprolactam by conversion to the hydroxamic acids and the subsequent phosgenation thereof. The yield reported in this document for the conversion of caprolactam to PDI is only about 32%.

WO 2008/015134 A1 claims a process for preparing PDI in which biobased lysine is converted to PDA, which is subsequently converted to PDI. The conversion of PDA to PDI can be effected in a phosgene-free manner or in the presence of phosgene, and the latter variant can be effected in the liquid phase or in the gas phase. Any impurities present in the PDI and measures for the avoidance or minimization thereof are not mentioned.

EP 2 684 867 A1 claims pentane 1,5-diisocyanate (PDI) having a content of 5-400 ppm of compounds (1) and (2) by cold-hot phosgenation of biobased pentane-1,5-diamine (PDA) or a salt thereof, a process for preparation thereof and polyisocyanates prepared thereby.

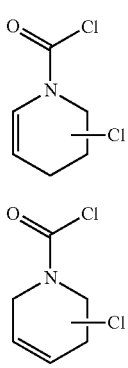

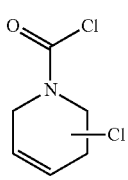

There is a description therein of the phosgenation of pentane-1,5-diamine salts, for example hydrochlorides, in inert solvents, for example o-dichlorobenzene, wherein the crude PDI thus obtained is conditioned to lower the content of compounds (1) and (2) prior to distillation by heating in the presence of an inert gas, for example nitrogen, and optionally a phosphorus compound, for example tris(tridecyl) phosphite, to 180-245° C. Nothing is said about the presence of the secondary component CPI or the removal thereof. This process also comprises several steps and requires long reaction times, which has an unfavorable effect on its economic viability.

There is therefore still a great need for a simple and inexpensive process for preparing PDI with sufficiently low contents of CPI, C6-Im and the two isomeric C6-Az species, which avoids the disadvantages of the prior art processes.

SUMMARY OF THE INVENTION

It has now been found that, surprisingly, crude PDI materials having already very low contents of CPI, C6-Im and the two isomeric C6-Az species can be obtained by reacting PDA with phosgene in the gas phase above its boiling temperature under specific conditions as described hereinafter.

These and other advantages and benefits of the present invention will be apparent from the Detailed Description of the Invention herein below.

DETAILED DESCRIPTION OF THE INVENTION

The present invention provides a process for preparing pentane 1,5-diisocyanate by reacting pentane-1,5-diamine (PDA) with phosgene in the gas phase, characterized in that
  a) the gas temperatures both of phosgene and of pentane-1,5-diamine (PDA) prior to entry into the reactor are in the range of 230-320° C. and
  b) the two reactant streams, and also an inert gas stream, are supplied to the reactor by means of an annular gap nozzle, the inert gas stream being supplied through the annular gap and hence between the two reactant streams,
  c) the reactant streams and the inert gas stream mix after entry into the reactor and
  d) then the amine and the phosgene react.

The phosgenation of amines in the gas phase is known per se and can be effected, for example, as described in EP 0 289 840 B1, EP 1 319 655 A2, EP 1 555 258 A1, EP 1 275 639 A1, EP 1 275 640 A1, EP 1 449 826 A1, EP 1 754 698 B1, DE 10 359 627 A1 or in the German patent application DE 10 2005 042392 A1.

Technical grade PDA having a purity of >99% and a water content of <500 ppm is used. It may originate from known processes, either from petrochemical-based production or from biobased production, for example from decarboxylation of lysine. PDA from biobased production is preferred.

Prior to performance of the process of the invention, the PDA is evaporated, heated to 230° C. to 320° C., preferably 270° C. to 310° C., and supplied to the reactor, preferably tubular reactor. It is possible for the PDA to be supplemented with an inert gas such as $N_2$, He, Ar or vapors of an inert solvent, for example aromatic hydrocarbons with or without halogen substitution.

Before being supplied to the reactor, the phosgene used in the phosgenation is heated, likewise to 230° C. to 320° C., preferably 270° C. to 310° C.

The two reactant streams and the inert gas stream are supplied to the reactor by means of an annular gap nozzle, as described, for example, in EP 1 555 258 A1. This patent application claims a process for preparing di- and triisocyanates in the gas phase in a tubular reactor having a twin-wall guide tube arranged centrally in the direction of its axis of rotation, with a concentric annular gap formed between the inner and outer walls of this twin-wall guide tube, the vaporous di- and/or triamines and phosgene are heated separately to temperatures of 200-600° C. and the amine stream is supplied to the tubular reactor through the concentric annular gap, while phosgene is supplied to the tubular reactor over the remaining cross-sectional area of the tubular reactor. The preparation of pentane 1,5-diisocyanate (PDI) is not described, nor are there any pointers therein to formation of chlorinated by-products or measures for avoidance or minimization thereof.

In the performance of the process of the invention, a tubular reactor is used, which likewise has a twin-wall guide tube arranged centrally in the direction of its axis of rotation, with a concentric annular gap formed between the inner and outer walls. By contrast with the procedure described in EP 1 555 258 A1, the preheated PDA stream, optionally diluted by an inert medium, is supplied here at a mean velocity of 20-150 m/s, preferably 20-100 m/s, through the inner twin-wall tube to the tubular reactor, while the preheated phosgene is supplied to the reactor over the remaining cross-sectional area between the outer twin-wall tube and the inner wall of the tubular reactor at a mean flow rate of at least 1 m/s, preferably 5-15 m/s. In addition, the two reactant streams, on entry into the reactor, are separated by an inert gas stream in the form of a cylindrical shell, which, after preheating to likewise 230° C. to 320° C., preferably 270° C. to 310° C., is supplied through the concentric annular gap of the twin-wall tube to the tubular reactor at a mean velocity of 20-150 m/s, preferably 20-100 m/s.

The annular gap nozzle to be used in accordance with the invention, since the inert gas stream separates the two reactant streams, is also referred to hereinafter as separation gap nozzle or nitrogen separation gap nozzle (using nitrogen as inert gas).

The inert gas stream may consist, for example, of nitrogen, noble gases such as helium or argon, or vapors of inert solvents. Preference is given to nitrogen. Suitable solvents are, for example, aromatic hydrocarbons with or without halogen substitution, for example chlorobenzene, o-dichlorobenzene, toluene, chlorotoluene, xylene, chloronaphthalene or decahydronaphthalene.

The flow rates of gaseous PDA and phosgene are chosen such that the molar phosgene excess, based on one amino group, is 30% to 300%, preferably 60% to 200%.

In the process of the invention, preference is given to using tubular reactors without internals and without moving parts in the interior of the reactor. The tubular reactors generally consist of steel, glass, alloyed or enameled steel, and the dimensions are such that complete reaction of the PDA with the phosgene is enabled under the process conditions. As described above, the gas streams are introduced into the tubular reactor at one end thereof via a separation gap nozzle. The mixing zone is preferably at a temperature within the range from 230° C. to 320° C., preferably 270° C. to 310° C., and this temperature can optionally be maintained by heating the tubular reactor.

In the performance of the process of the invention, in general, the pressure in the inlets to the reaction space is 200-3000 mbar abs., preferably 800-1500 mbar abs., and at the outlet from the reaction space is 150-2000 mbar abs., preferably 750-1440 mbar abs., with observation of a flow rate within the reaction space of 3 to 120 m/s, preferably 5 to 75 m/s, by maintaining a suitable pressure differential. Under these prerequisites, turbulent flow conditions generally exist within the reaction space.

The dwell time of the reaction mixture in the reactor is 0.1 to 1 seconds, preferably 0.2 to 0.5 seconds. The dwell time is calculated from the throughput of the reactant streams per unit time, the dimensions of the reactor and the reaction parameters of pressure and temperature.

On completion of the phosgenation reaction in the reaction space, the gaseous mixture continuously leaving the reaction space is freed of the PDI formed. This can be effected, for example, with the aid of an inert solvent, the temperature of which is chosen such that it is, on the one hand, above the breakdown temperature of the carbamoyl chloride corresponding to the PDI and, on the other hand, below the condensation temperature of the PDI and preferably also of any solvent used as diluent in vaporous form, such that PDI and auxiliary solvent condense or dissolve in the auxiliary solvent, while excess phosgene, hydrogen chloride and any inert gas used as diluent pass through the condensation stage or the solvent in gaseous form. Particularly suitable solvents for selectively obtaining the PDI from the mixture leaving the reaction space in gaseous form are solvents of the type mentioned by way of example above that are kept at a temperature of 60 to 200° C., preferably 90 to 170° C., especially technical grade monochlorobenzene (MCB) and dichlorobenzene (ODB). Preference is given to MCB. Conceivable methods of selective condensation of isocyanate formed out of the gas mixture leaving the reactor using solvents of this kind are, for example, the passing of the gas mixture through the solvent mentioned or the injection of the solvent (solvent mist) into the gas stream (quench).

The gas mixture that passes through the condensation stage for obtaining the PDI is subsequently freed of excess phosgene in a manner known per se. This can be effected by means of a cold trap, absorption in an inert solvent (e.g. chlorobenzene, MCB, or dichlorobenzene, ODB) kept at a temperature of −10° C. to 8° C., or adsorption and hydrolysis on activated carbon. The hydrogen chloride gas that passes through the phosgene recovery stage can be recycled in a manner known per se to recover the chlorine required for phosgene synthesis.

The preparation of pure PDI is preferably effected by distillative workup of the crude PDI solution in the solvent used for isocyanate condensation.

The advantages of the process of the invention are:
a) Low by-product formation and hence low contents of chlorinated by-products even in the crude materials. Excluding the solvent from the calculation, the concentrations of CPI are <0.5% by weight, preferably <0.3% by weight, and the sum total of C6-Im and C6-Az is <400 ppm, preferably <350 ppm. In this way, it is possible to keep the cost and inconvenience associated with the subsequent distillation at a low level.
b) Avoidance of solid deposits on the reactor wall and in the quench.

The present invention provides a process for preparing pentane 1,5-diisocyanate (PDI) by reacting pentane-1,5-diamine (PDA) with phosgene in the gas phase, characterized in that
a) the gas temperatures both of phosgene and of pentane-1,5-diamine (PDA) prior to entry into the reactor are in the range of 230-320° C. and
b) the two reactant streams, and also an inert gas stream, are supplied to the reactor by means of an annular gap nozzle, the inert gas stream being supplied through the annular gap and hence between the two reactant streams,
c) the reactant streams and the inert gas stream mix after entry into the reactor and
d) then the amine and the phosgene react.

In a second embodiment of the process, the temperature of the PDA in a) is in the range from 270° C. to 310° C.

In a third embodiment, the process according to embodiment 1 or 2 is conducted such that the temperature of the phosgene in a) is within the range from 270° C. to 310° C.

In a third embodiment, the process according to any of embodiments 1 to 3 is conducted such that the flow rates of gaseous PDA and phosgene are chosen such that the molar phosgene excess based on one amino group is 30% to 300%.

In a fourth embodiment, the process according to any of embodiments 1 to 3 is conducted such that the flow rates of gaseous PDA and phosgene are chosen such that the molar phosgene excess based on one amino group is 60% to 200%.

In a fifth embodiment, the process according to any of embodiments 1 to 4 is conducted in such a way that the pressure in the inlets to the reaction space is 200-3000 mbar abs. and the pressure at the outlet from the reaction space is 150-2000 mbar abs.

In a sixth embodiment, the process according to any of embodiments 1 to 4 is conducted in such a way that the pressure in the inlets to the reaction space is 800 to 1500 mbar abs. and the pressure at the outlet from the reaction space is 750 to 1440 mbar abs.

In a seventh embodiment, the process according to any of embodiments 1 to 6 is conducted in such a way that the dwell time of the reaction mixture in the reactor is 0.1 to 1 seconds.

In an eighth embodiment, the process according to any of embodiments 1 to 6 is conducted in such a way that the dwell time of the reaction mixture in the reactor is 0.2 to 0.5 seconds.

EXAMPLES

GC Method of PDI Analysis:

| | |
|---|---|
| Gas chromatograph: | Agilent (formerly Hewlett PACKARD), 7890, Series A or B (6890 Series A or B are also possible), |

-continued

| Separation column: | RXI 17 (Restek), fused silica, length 30 m, internal diameter 0.32 mm, film thickness 1.0 µm | |
|---|---|---|
| Temperatures: | injector 250° C., detector (FID) 350° C. | |
| Oven: | Start 80° C., hold time 0 min, Heating rate 10K/min to 140° C., hold time 7.5 min Heating rate 20K/min to 250° C., hold time 5.0 min Run time 24 min | |
| Carrier gas: | hydrogen | |
| | Gas setting | constant flow rate rather than constant pressure |
| | Column pressure | about 0.4 bar abs., at start of analysis |
| | Column flow | about 100 mL/min at constant flow rate |
| | Split | flow rate 100 mL/min Ratio of 50:1 |
| | Septum purge | about 3 mL/min |

Comparative Example 1

Liquid Phase Phosgenation of PDA in MCB (Noninventive)

A 2 L four-neck flask with stirrer, thermometer, reflux condenser, dropping funnel and gas inlet tube was initially charged with 463 g of MCB, and 437 g of phosgene were condensed in at −5° C. While stirring and cooling, a solution of 75 g of PDA in 416 g of MCB was added dropwise within 30 minutes, in the course of which the temperature was kept between 0-8° C. After the addition had ended, the cooling was removed and the reaction mixture was heated gradually up to reflux with further introduction of phosgene within 2 hours, with occurrence of significant evolution of gas within the temperature range of 40-80° C. Subsequently, phosgenation was effected for a further 12 hours under reflux. The reaction mixture was freed of phosgene by blowing with nitrogen and filtered, and the filter residue was washed repeatedly with MCB. The filter residue was dried and weighed, while the combined filtrates were largely freed of the solvent by vacuum distillation by means of a Rotavapor. The following were obtained:

Solids: 17.3 g; crude solution: 97.7 g containing 9% MCB
Yield: 56.7% of theory of PDI
GC analysis (excluding MCB, area percent (area %)):

| CPI | 1.432 |
|---|---|
| C6-Az | 0.409 |
| C6-Im | 0.000 |
| PDI | 98.159 |

Comparative Example 2

Liquid Phase Phosgenation of PDA in ODB (Noninventive)

Analogously to Comparative Example 1, 75 g of PDA were converted in ODB, keeping the amount of solvent and reaction times and temperatures the same. The following were obtained:

Solids: 14.8 g; crude solution: 85.5 g containing 17% ODB
Yield: 44.0% of theory of PDI GC analysis (excluding MCB, area %):

| CPI | 4.047 |
|---|---|
| C6-Az | 0.000 |
| C6-Im | 0.508 |
| PDI | 95.445 |

Comparative Example 3

Gas Phase Phosgenation of PDA at 340° C. with Coaxial Nozzle (Simple Smooth Jet Nozzle) (Noninventive)

In a plant for gas phase phosgenation with an amine evaporation stage, a tubular reactor (L: 1770 mm, internal diameter 37 mm) having a coaxial nozzle (internal diameter 6.5 mm) arranged on the reactor axis and a downstream isocyanate condensation stage, at a pressure of 1300 mbar abs., measured at the end of the isocyanate condensation stage, 6.88 kg/h of PDA were evaporated continuously with introduction of a nitrogen stream of 0.138 kg/h, superheated to 340° C. and fed to the reactor via the coaxial nozzle. Simultaneously and in parallel thereto, 36.6 kg/h of phosgene were heated to 340° C. and, in the annular space left clear by the nozzle, likewise continuously supplied to the reactor in which the two reactant streams were mixed and brought to reaction. The velocity of the gas stream in the reactor is about 6.8 m/s and the velocity ratio of the amine/nitrogen stream to the phosgene stream was 5.9. After an average residence time in the reactor of 0.26 seconds the gas stream containing the reaction product PDI was cooled by injection cooling with monochlorobenzene and condensed, the temperature of the liquid phase in the quench being about 90° C. After only 4 hours, the plant had to be shut down owing to a pressure rise because of fouling in the nozzle and in the reactor.

The GC analysis of the crude solution obtained showed the following composition (excluding MCB, area %):

| CPI | 0.499 |
|---|---|
| C6-Az | 0.195 |
| C6-Im | 3.893 |
| PDI | 95.414 |

Comparative Example 4

Gas Phase Phosgenation of PDA at 310° C. with Coaxial Nozzle (Noninventive)

The phosgenation was conducted as described in Example 3, with heating both of the nitrogen-diluted gaseous PDA and of the phosgene to 310° C. prior to entry into the reactor. The velocity of the gas stream in the reactor was about 6.5 m/s, the velocity ratio of the amine/nitrogen stream to the phosgene stream was 6.0 and the mean residence time in the reactor was 0.27 seconds. Here, the plant had to be shut down after 7 hours owing to a pressure rise because of fouling in the nozzle and in the reactor.

The GC analysis of the crude solution obtained showed the following composition (excluding MCB, area %):

| | |
|---|---|
| CPI | 0.823 |
| C6-Az | 0.098 |
| C6-Im | 1.060 |
| PDI | 98.019 |

Comparative Example 5

Gas Phase Phosgenation of PDA at 340° C. with Nitrogen Separation Gap Nozzle Nozzle (Noninventive)

In a plant for gas phase phosgenation with an amine evaporation stage, a tubular reactor (L: 1770 mm, internal diameter 37 mm) having a separation gap nozzle (internal diameter 6.5 mm, separation gap: internal diameter 6.5 mm, external diameter 8.5 mm) arranged on the reactor axis and a downstream isocyanate condensation stage, at a pressure of 1300 mbar abs., measured at the end of the isocyanate condensation stage, 8.46 kg/h of PDA were evaporated continuously, superheated to 340° C. and fed to the reactor via the inner central nozzle. Simultaneously and in parallel thereto, 1.48 kg/h of nitrogen and 45 kg of phosgene were heated to 310° C. and, through the separation gap (nitrogen) or through the annular space left clear by the nozzle (phosgene), likewise continuously supplied to the reactor in which the two reactant streams were mixed and brought to reaction. The velocity of the gas stream in the reactor was about 8.9 m/s and the velocity ratio of the amine/nitrogen stream to the phosgene stream was 5.59. After a mean residence time in the reactor of 0.20 seconds, the gas stream containing the reaction product PDI was cooled by injection cooling with monochlorobenzene and condensed, the temperature of the liquid phase in the quench being about 90° C. The plant was operated without any problem over a period of 60 hours. Thereafter, the pressure rose gradually, and so the plant had to be shut down after 66 hours because of fouling in the reactor.

The GC analysis of the crude solution obtained showed the following composition (excluding MCB, area %):

| | |
|---|---|
| CPI | 0.423 |
| C6-Az | 0.098 |
| C6-Im | 0.360 |
| PDI | 99.119 |

Example 1

Gas Phase Phosgenation of PDA at 310° C. with Nitrogen Separation Gap Nozzle (Inventive)

The phosgenation was conducted as described in Comparative Example 5, with heating of PDA, nitrogen and phosgene to 310° C. prior to entry into the reactor. The velocity of the gas stream in the reactor was about 8.5 m/s, the velocity ratio of the amine/nitrogen stream to the phosgene stream was 6.0 and the mean residence time in the reactor was 0.21 seconds. The plant was operated without any problem over a period of 100 hours. After shutdown and opening of the plant, the nozzle and reactor did not have any soiling.

The GC analysis of the crude solution obtained showed the following composition (excluding MCB, area %):

| | |
|---|---|
| CPI | 0.286 |
| C6-Az | 0.032 |
| C6-Im | 0.004 |
| PDI | 99.678 |

In the liquid phase phosgenation of PDA (base phosgenation) in MCB and ODB (Comparative Examples 1 and 2), very poor yields are obtained and very high proportions of CPI are formed.

In the gas phase phosgenation with the coaxial nozzle (simple smooth jet nozzle), prohibitively high proportions of C6-Im are formed at 340° C. (Comparative Example 3). Even at 310° C. (Comparative Example 4), the C6-Im contents are still relatively high. Moreover, in Comparative Examples 3 and 4, only very short plant operation times are achieved because of fouling in the nozzle and reactor.

In gas phase phosgenation with the nitrogen separation nozzle, high C6-Im contents still form at 340° C. (Comparative Example 5). The operation time is improved, but still unsatisfactory.

Example 1 shows that, through the combination of the use of a nitrogen separation gap nozzle and reactant temperatures of 310° C. of PDA, nitrogen and phosgene prior to entry into the reactor, it is possible to distinctly reduce the proportions of chlorinated by-products, and no fouling occurs any longer even after a prolonged plant operation time.

Various aspects of the subject matter described herein are set out in the following numbered clauses:

1. A process for preparing pentane 1,5-diisocyanate (PDI) by reacting pentane-1,5-diamine (PDA) with phosgene in the gas phase, characterized in that a) the gas temperatures both of phosgene and of pentane-1,5-diamine (PDA) prior to entry into the reactor are in the range of 230-320° C. and b) the two reactant streams, and also an inert gas stream, are supplied to the reactor by means of an annular gap nozzle, the inert gas stream being supplied through the annular gap and hence between the two reactant streams, c) the reactant streams and the inert gas stream mix after entry into the reactor and d) then the amine and the phosgene react.

2. The process for preparing pentane 1,5-diisocyanate (PDI) as in clause 1, wherein technical grade PDA having a purity of >99% and a water content of <500 ppm is used.

3. The process for preparing pentane 1,5-diisocyanate (PDI) as in clause 2, wherein the PDA originates from biobased production.

4. The process for preparing pentane 1,5-diisocyanate (PDI) as in any of clauses 1 to 3, wherein the temperature of the PDA in a) is in the range from 270° C. to 310° C.

5. The process for preparing pentane 1,5-diisocyanate (PDI) as in any of clauses 1 to 4, wherein the temperature of the phosgene in a) is in the range from 270° C. to 310° C.

6. The process for preparing pentane 1,5-diisocyanate (PDI) as in any of clauses 1 to 5, wherein the flow rates of gaseous PGA and phosgene are chosen such that the molar phosgene excess based on one amino group is 30% to 300%.

7. The process for preparing pentane 1,5-diisocyanate (PDI) as in any of clauses 1 to 6, wherein the annular gap nozzle is formed by a tubular reactor having a twin-wall guide tube arranged centrally in the direction of its axis of rotation, wherein a concentric annular gap is formed between the inner and outer walls.

8. The process for preparing pentane 1,5-diisocyanate (PDI) as in any of clauses 1 to 7, wherein the inert gas stream in c) consists of nitrogen, a noble gas, vapors of an inert solvent or mixtures of these inert gases.

9. The process for preparing pentane 1,5-diisocyanate (PDI) as in any of clauses 1 to 8, wherein the pressure in the inlets to the reaction space is 200-3000 mbar abs.

10. The process for preparing pentane 1,5-diisocyanate (PDI) as in any of clauses 1 to 9, wherein the pressure at the outlet from the reaction space is 150-2000 mbar abs.

11. The process for preparing pentane 1,5-diisocyanate (PDI) as in any of clauses 1 to 10, wherein the dwell time of the reaction mixture in the reactor is 0.1 to 1 second.

The invention claimed:

1. A process for preparing pentane 1,5-diisocyanate (PDI) by reacting a stream of pentane-1,5-diamine (PDA) with a stream of phosgene in the gas phase, the process comprising:
    a) increasing the temperatures both of the phosgene stream and of the pentane-1,5-diamine (PDA) stream prior to entry into a reactor to 230-320° C.;
    b) supplying the pentane-1,5-diamine (PDA) stream and the phosgene stream, and an inert gas stream to the reactor by an annular gap nozzle, with the inert gas stream being supplied through the annular gap;
    c) mixing the pentane-1,5-diamine (PDA) stream, the phosgene stream and the inert gas stream after entry into the reactor and
    d) reacting the amine and the phosgene,
wherein the concentration of 5-chloropentyl isocyanate (CPI) is <0.5% by weight based on the weight of the PDI, excluding solvent.

2. The process for preparing pentane 1,5-diisocyanate (PDI) according to claim 1, wherein the PDA has a purity of >99% and a water content of <500 ppm.

3. The process for preparing pentane 1,5-diisocyanate (PDI) according to claim 2, wherein the PDA originates from biobased production.

4. The process for preparing pentane 1,5-diisocyanate (PDI) according to claim 1, wherein the temperature of the PDA in a) is from 270° C. to 310° C.

5. The process for preparing pentane 1,5-diisocyanate (PDI) according to claim 1, wherein the temperature of the phosgene in a) is from 270° C. to 310° C.

6. The process for preparing pentane 1,5-diisocyanate (PDI) according to claim 1, wherein the flow rates of gaseous PGA and phosgene are such that the molar phosgene excess based on one amino group is 30% to 300%.

7. The process for preparing pentane 1,5-diisocyanate (PDI) according to claim 1, wherein the annular gap nozzle is formed by a tubular reactor having a twin-wall guide tube arranged centrally in the direction of its axis of rotation, and wherein a concentric annular gap is formed between the inner and outer walls.

8. The process for preparing pentane 1,5-diisocyanate (PDI) according to claim 1, wherein the inert gas stream in c) is selected from the group consisting of nitrogen, a noble gas, vapors of an inert solvent or mixtures of these inert gases.

9. The process for preparing pentane 1,5-diisocyanate (PDI) according to claim 1, wherein the pressure in an inlet to the reaction space is 200-3000 mbar abs.

10. The process for preparing pentane 1,5-diisocyanate (PDI) according to claim 1, wherein the pressure at an outlet from the reaction space is 150-2000 mbar abs.

11. The process for preparing pentane 1,5-diisocyanate (PDI) according to claim 1, wherein dwell time in the reactor is 0.1 to 1 seconds.

* * * * *